United States Patent
Yoon et al.

(10) Patent No.: US 11,198,019 B2
(45) Date of Patent: Dec. 14, 2021

(54) OPTICAL OUTPUT DEVICE FOR SKIN CARE

(71) Applicant: LG ELECTRONICS INC., Seoul (KR)

(72) Inventors: Byoungho Yoon, Seoul (KR); Jooyong Kim, Seoul (KR); Byungwon Cho, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 16/639,280

(22) PCT Filed: May 15, 2018

(86) PCT No.: PCT/KR2018/005551
§ 371 (c)(1),
(2) Date: Feb. 14, 2020

(87) PCT Pub. No.: WO2019/035535
PCT Pub. Date: Feb. 21, 2019

(65) Prior Publication Data
US 2020/0246631 A1    Aug. 6, 2020

(30) Foreign Application Priority Data
Aug. 14, 2017   (KR) .................. 10-2017-0102904

(51) Int. Cl.
*A61N 5/06*    (2006.01)

(52) U.S. Cl.
CPC .... *A61N 5/0616* (2013.01); *A61N 2005/0627* (2013.01); *A61N 2005/0628* (2013.01);
(Continued)

(58) Field of Classification Search
CPC .......... A61N 5/0616; A61N 2005/0628; A61N 2005/0652; A61N 2005/0663; A61N 2005/0627; A61N 2005/0647
See application file for complete search history.

(56) References Cited

U.S. PATENT DOCUMENTS

| | | | |
|---|---|---|---|
| 10,286,224 B2 | 5/2019 | Tapper et al. | |
| 2007/0208395 A1* | 9/2007 | Leclerc | A61N 5/0616 607/86 |
| 2016/0038763 A1* | 2/2016 | Tapper | A61N 5/0616 607/88 |

FOREIGN PATENT DOCUMENTS

| KR | 10-2007-0053408 | 5/2007 |
|---|---|---|
| KR | 1020070053408 | 5/2007 |

(Continued)

OTHER PUBLICATIONS

PCT International Application No. PCT/KR2018/005551, International Search Report dated Aug. 9, 2018, 3 pages.
(Continued)

*Primary Examiner* — Brian T Gedeon
*Assistant Examiner* — Joshua Andrew Schum-Houck
(74) *Attorney, Agent, or Firm* — Lee, Hong, Degerman, Kang & Waimey PC (57) ABSTRACT

An optical output device for skin care, according to an embodiment of the present disclosure, comprises: a substrate disposed such that at least one light source is oriented toward a user's skin; a front cover covering one surface of the substrate; a rear cover covering the other surface of the substrate; a wearing device coupled to the rear cover so as to make contact with a part of the user's body such that the optical output device for skin care is worn by the user; and a wearing detection sensor for detecting whether the user is wearing the device.

10 Claims, 9 Drawing Sheets

(52) U.S. Cl.
CPC .............. *A61N 2005/0647* (2013.01); *A61N 2005/0652* (2013.01)

(56) References Cited

FOREIGN PATENT DOCUMENTS

| | | | |
|---|---|---|---|
| KR | 1020110117481 | 10/2011 | |
| KR | 20120024495 | 3/2012 | |
| KR | 20-0471948 | 3/2014 | |
| KR | 1020140075706 | 6/2014 | |
| KR | 101635927 | 7/2016 | |
| KR | 20160095878 | 8/2016 | |
| KR | 101720879 | 3/2017 | |
| KR | 101735703 | 5/2017 | |
| WO | WO-2014162271 A2 * | 10/2014 | ........... A61N 5/0618 |
| WO | WO-2015140474 A1 * | 9/2015 | ......... A61H 15/0085 |

OTHER PUBLICATIONS

Korean Intellectual Property Office Application No. 10-2019-0079711, Office Action dated Sep. 30, 2019, 5 pages.
Korean Intellectual Property Office Application No. 10-2018-0040903, Notice of Allowance dated Feb. 24, 2021, 26 pages.

* cited by examiner

OPTICAL OUTPUT DEVICE FOR SKIN CARE

CROSS-REFERENCE TO RELATED APPLICATIONS

This application is the National Stage filing under 35 U.S.C. 371 of International Application No. PCT/KR2018/005551, filed on May 15, 2018, which claims the benefit of earlier filing date and right of priority to Korean Application No. 10-2017-0102904, filed on Aug. 14, 2017, the contents of which are all hereby incorporated by reference herein in their entirety.

TECHNICAL FIELD

The present disclosure relates to an optical output device for skin care, and more particularly, to a device for outputting light to a facial skin worn on a user's face.

BACKGROUND ART

A skin may be damaged due to aging of cells, repetition of certain facial expressions, constant exposure to external environments (ultraviolet rays, fine dust, etc.), and stress. For example, the aging of cells or the repetition of the certain facial expressions may cause wrinkles on the skin, and the continuous exposure or the stress to the external environments may cause various troubles such as acne and blemishes.

The skin care for preventing or minimizing the damage to the skin is aimed at maintenance of blemish-free, clean and smooth skin, and in particular, the greatest interest has been in caring the skin of the face among the body parts. Therefore, people try to keep their clean skin by receiving massage, applying a functional cosmetic product, or using various cleaning products to care for the facial skin.

In particular, recently, a device (e.g., a mask-type skin care device) attached or worn on the user's face to output light has emerged. A plurality of light sources (e.g., LEDs) may be disposed in the optical output device to output light toward the user's face skin or the like.

When the plurality of light sources are arranged to output light, if the output light is not uniformly irradiated to the user's skin, an effect of the skin care may be deteriorated. Alternatively, in the case of a specific area such as the forehead, the skin damage may be more severe than in other areas. Int this case, it is necessary to focus more light onto the specific area.

DISCLOSURE OF THE INVENTION

Technical Problem

An object of the present disclosure is to provide an optical output device for skin care that is capable of operating by effectively detecting whether the user is wearing.

Another object of the present disclosure is to provide an optical output device for skin care having a structure for irradiating light having different intensities according to skin parts.

Further another object of the present disclosure is to provide an optical output device for skin care, in which light output from a plurality of light sources is evenly irradiated to a user's skin.

Technical Solution

An optical output device for skin care according to an embodiment of the present disclosure includes a substrate disposed so that at least one light source is oriented toward a user's skin, a front cover configured to cover one surface of the substrate, a rear cover configured to cover the other surface of the substrate, a wearing device coupled to the rear cover to contact a portion of a user's body so that the optical output device for the skin care is worn on the user, and a wearing detection sensor configured to detect whether the user is wearing.

The wearing device may include a first opening and a second opening, which are defined in positions corresponding to a left eye and a right eye of the user, a first face contact part and a second face contact part, which are disposed along boundaries of the openings to contact a skin of the user, and a nose seating part disposed between the openings so as to be seated on a nose of the user, wherein the wearing detection sensor may be disposed between the first opening and the second opening.

According to some embodiments, the wearing detection sensor may be provided in the nose seating part or on a surface of the nose seating part.

Each of the substrate, the front cover, the rear cover, and the wearing device may have an opening for securing a user's view, and the opening defined in the substrate may have a size greater than or equal to that of each of the remaining openings.

The optical output device may further include a controller configured to control an operation of each of the at least one light source and the wearing detection sensor, wherein the controller may be configured to detect whether the user is wearing based on a detection signal received from the wearing detection sensor and control the at least one light source so that the light source emits light based on the detected result.

The controller may be provided on the substrate or in a user operation device connected to the substrate.

A plurality of light sources may be disposed to be spaced apart from each other on the substrate, and the plurality of light sources may emit different light based on an operation mode of the optical output device for the skin care.

The rear cover may include a groove configured to disperse the light emitted from the plurality of light sources and a plurality of lenses disposed to correspond to positions of the plurality of light sources, respectively.

A portion of the plurality of lenses is implemented as a convex lens so that the light emitted from the light source is concentrated and irradiated to a predetermined position.

The rear cover may include a light guide layer configured to scatter the light emitted from the at least one light source, and the light guide layer may include a plurality of scattering particles.

The rear cover may include an opening for securing the user's view, and at least one light absorption part may be disposed along a boundary of the opening on a surface of both surfaces of the rear cover, which faces the substrate.

Advantageous Effects

According to the embodiment of the present disclosure, the optical output device for the skin care may be provided with the wearing detection sensor at a position at which the difference according to the user's face shape such as the head and nose is minimized to more accurately and effectively detect the user's wearing.

Also, the size of the openings formed in the substrate among the openings of the optical output device for the skin care may be formed to be greater than or equal to the remaining openings, thereby preventing the light source from being disposed in close proximity to the left and right eyes of the user. In addition, the light absorption part made of the material having the high light absorption rate may be disposed in the opening of the rear cover to effectively absorb the light irradiated to the left and right eyes of the user. Therefore, the risk of the discomfort or damage of the eye due to the irradiation of the light to the left and right eyes may be prevented.

In addition, the groove or the light guide layer that disperses or scatters the light emitted from the light sources of the substrate may be formed on the rear cover to improve the skin care effect by allowing the light to be evenly irradiated to the skin of the user.

Also, the convex lens may be disposed at the position corresponding to the specific part such as the forehead or cheek in which a lot of wrinkles or troubles occur in the rear cover to maximize the skin care effect by concentrating the light to the corresponding part.

MODE FOR CARRYING OUT THE DISCLOSURE

Hereinafter, embodiments disclosed in this specification is described with reference to the accompanying drawings, and the same or corresponding components are given with the same drawing number regardless of reference number, and their duplicated description will be omitted. Furthermore, terms, such as a "module" ad a "unit", are used for convenience of description, and they do not have different meanings or functions in themselves. Moreover, detailed descriptions related to well-known functions or configurations will be ruled out in order not to unnecessarily obscure subject matters of the present disclosure. However, this does not limit the present disclosure within specific embodiments and it should be understood that the present disclosure covers all the modifications, equivalents, and replacements within the idea and technical scope of the present disclosure.

It will be understood that although the ordinal numbers such as first and second are used herein to describe various elements, these elements should not be limited by these numbers. The terms are only used to distinguish one component from other components.

It will also be understood that when an element is referred to as being "'connected to" or "engaged with" another element, it can be directly connected to the other element, or intervening elements may also be present. It will also be understood that when an element is referred to as being 'directly connected to' another element, there is no intervening elements.

The terms of a singular form may include plural forms unless referred to the contrary.

In this application, the terms "comprises" or "having" are intended to indicate that there is a feature, number, step, operation, component, part, or combination thereof described in the specification, and one or more other features. It is to be understood that the present disclosure does not exclude the possibility of the presence or the addition of numbers, steps, operations, components, components, or a combination thereof.

Hereinafter, exemplary embodiments of the present disclosure will be described in detail with reference to the accompanying drawings.

Figure 1:
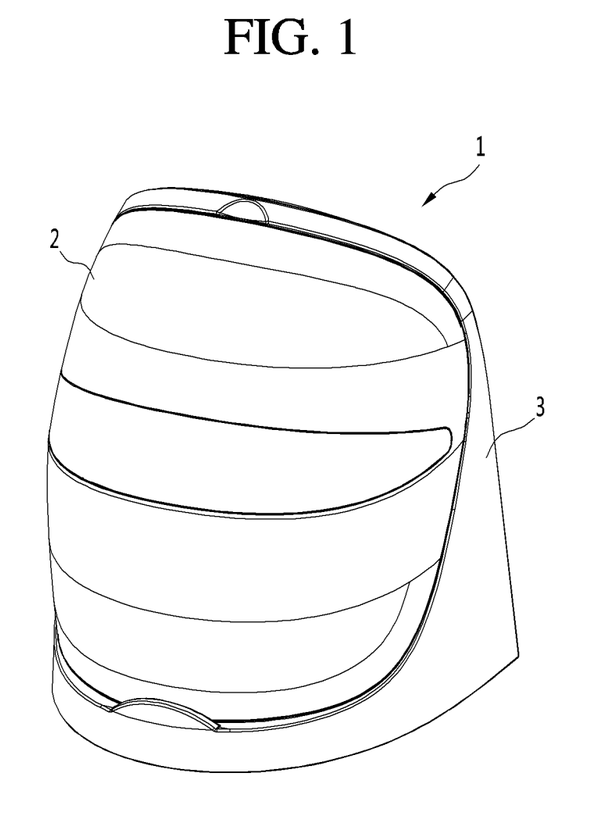
FIG. 1 is a perspective view of a package including an optical output device for skin care and cradles according to an embodiment of the present disclosure.
Figure 2:
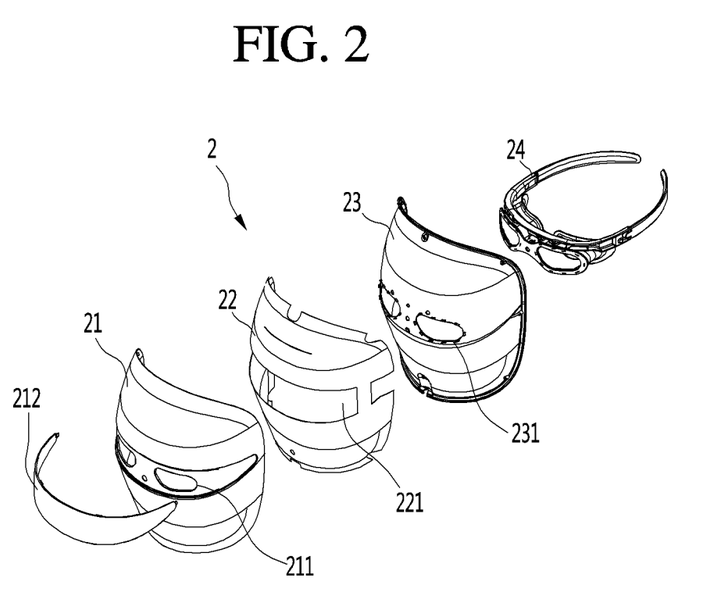
FIG. 2 is an exploded perspective view of the optical output device for the skin care according to an embodiment of the present disclosure.
Figure 3:
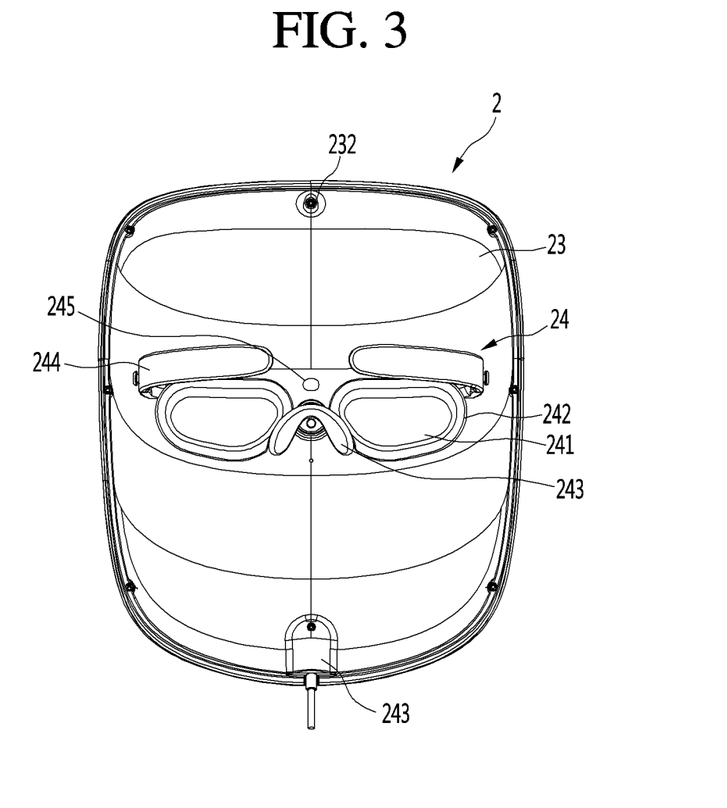
FIG. 3 is a rear view of the optical output device for the skin care according to an embodiment of the present disclosure.
Figure 4:
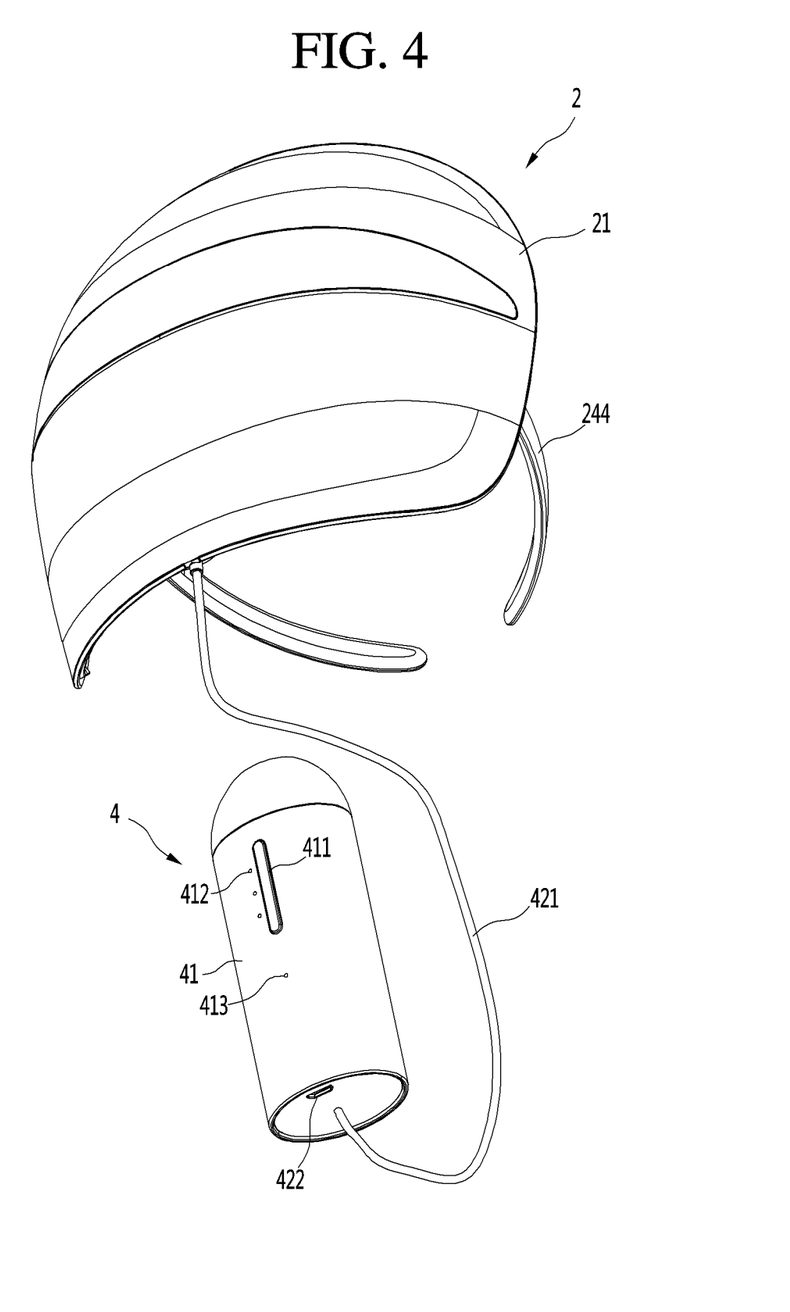
FIG. 4 is a perspective view of the optical output device for the skin care and a user operation device according to an embodiment of the present disclosure.

FIG. 1 is a perspective view of a package including an optical output device for skin care and cradles according to an embodiment of the present disclosure, and FIG. 2 is an exploded perspective view of the optical output device for the skin care according to an embodiment of the present disclosure. FIG. 3 is a rear view of the optical output device for the skin care according to an embodiment of the present disclosure, and FIG. 4 is a perspective view of the optical output device for the skin care and a user operation device according to an embodiment of the present disclosure.

Referring to FIG. 1, an optical output device 2 for skin care (hereinafter, referred to as an "optical output device") according to an embodiment of the present disclosure may be a device that is worn on a portion of a user's body to output light to a user's skin, thereby promoting activity of skin cells to improve wrinkles, elasticity, skin tone, or reduce skin troubles. The optical output device 2 may constitute one skin care package 1 together with a cradle 3 that is mounted when the optical output device is charged or stored. As the cradle 3 is mounted, a battery (not shown) provided in the optical output device 2 may be charged by power supplied from the cradle 3.

The optical output device 2 according to an embodiment of the present disclosure may correspond to a mask type device that is worn on a user's face to output light to the user's face skin. In order to evenly output the light throughout the user's face skin, the optical output device 2 may be rounded along a shape of the face of a person.

The cradle 3 may be connected to the optical output device 2 to supply the power for the charging to the optical output device 2 or the battery (not shown) provided in the user operation device 4 connected to the optical output device 2. For this, the cradle 3 may be connected to an external power supply to receive power from the outside.

The cradle 3 may provide a seating part for mounting the optical output device 2. As illustrated in FIG. 1, the cradle 3 may have the seating part formed to correspond to an outer edge of the optical output device 2, but this is not necessarily limited thereto.

Referring to FIG. 2, the optical output device 2 may include a front cover 21, a substrate 22, a rear cover 23, and a wearing device 24.

The front cover 21 may define an entire surface of the optical output device 2 and protect the substrate 22 provided between the front cover 21 and the rear cover 23 from an external shock, a contact, and the like. For this, the front cover 21 may be implemented with various plastics, ceramics, and the like.

An opening 211 for securing a user's view when worn by the user may be defined in the front cover 21. When the user wears the optical output device 2, the user's eyes are located in the opening 211, and thus the user may secure the user's view through the opening 211. According to an embodiment, in order to prevent foreign substances from contacting or colliding with the user's eyes through the opening 211, an opening protection cover 212 covering the opening 211 may be provided. The opening protection cover 212 may be made of acrylic, plastic, or the like that is a transparent material.

The substrate 22 may include at least one light source that emits light for the skin care of the user. According to an embodiment, in order to output light having different colors according to an operation mode of the optical output device 2, the at least one light source may include a plurality of LEDs for outputting light having different colors.

For example, the plurality of LEDs may include at least one red LED and at least one blue LED. The red LED may emit red light at a wavelength of about 645 nm to about 670 nm. The red light may promote activity of skin cells, which is effective in improving wrinkles, elasticity, and skin tone. The blue LED may emit blue light at a wavelength of about 400 nm to about 430 nm. The blue light may be effective for removing various troubles of the skin.

If it is assumed that the operation mode of the optical output device 2 is divided into an active promotion mode and a trouble removal mode, when the operation mode is set to the active promotion mode, the red LED may be activated to emit the red light to the skin. On the other hand, when the operation mode is set to the trouble removal mode, the blue LED may be activated to emit the blue light to the skin. A control of the light source according to the operation mode may be performed by a controller of the optical output device 2 to be described later. According to an embodiment, the plurality of LEDs may further include at least one yellow LED. The yellow LED may emit yellow light at a wavelength of about 580 nm to about 600 nm, and the yellow light may be effective to brighten skin tones.

The substrate 22 may include a controller for controlling the light output operation of the at least one light source. The controller may be implemented as an integrated circuit (IC), a microcomputer, an embedded processor, an application processor (AP), or the like. According to an embodiment, the controller may be provided in the user operation device 4 to be described later.

Similar to the front cover 21, an opening 221 for securing the user's view when the user is wearing may be defined in the substrate 22. As described above, when the user wears the optical output device 2, the user's eyes are located in the opening 221, and thus the user may secure the user's view through the opening 221.

The substrate 22 provided in the optical output device 2 having a mask shape may be formed so that at least a portion thereof has a curved surface. For this, the substrate 22 may be made of a plastic material or the like.

The rear cover 23 may be coupled to the front cover 21 and the substrate 22 to cover one surface of the substrate 22. The front cover 21 and the rear cover 23 may prevent water or other foreign substances from permeated into the substrate 22 disposed therein, thereby preventing the light source or other components disposed on the substrate 22 from being broken down or damaged.

Also, when the user wears the optical output device 2, the rear cover 23 may be disposed between the substrate 22 and the user's skin to prevent the user's skin from contacting the substrate 22.

The rear cover 23 may be made of transparent plastic, acrylic, or the like so that the light emitted from the light source provided in the substrate 22 is irradiated to the user's face skin. In particular, the rear cover 23 may have a structure that allows the light emitted from the light source to be evenly irradiated to the skin or allows the light to be concentrated to a specific site.

Like the front cover 21 and the substrate 22, the rear cover 23 may also include an opening 231 for securing the user's view.

The wearing device 24 may fix the optical output device 2 to the user as the user wears the optical output device 2. The wearing device 24 may be coupled to the rear cover 23. For example, the wearing device 24 may have a shape of glasses that are seated and worn on the nose and ears of the user.

In particular, the wear device 24 according to an embodiment of the present disclosure may include a wearing detection sensor for effectively detecting whether the user is wearing.

More specific structure and configuration of the wearing device 24 will be described with reference to FIG. 3.

Referring to FIG. 3, the wearing device 24 may include an opening 241, a face contact part 242, a nose seating part 243, a wearing fixing part 244, and a wearing detection sensor 245.

Like the front cover 21, the substrate 22, and the rear cover 23, the opening 241 may be defined to secure the user's view when the user is wearing. The opening 241 may include a first opening and a second opening, which are defined in positions corresponding to the left and right eyes of the user, respectively. According to an embodiment, when the opening protection cover 212 is not provided in the front cover 21, a lens may be provided in the opening 241 of the wearing device 24. The phenomenon in which the foreign substances are prevented from contacting or colliding with the user's eyes by the opening protection cover 212 or the lens.

When comparing the openings respectively defined in the front cover 21, the substrate 22, the rear cover 23, and the wearing device 24, the opening 221 defined in the substrate 22 may have a size greater than or equal to that of each of the remaining openings 211, 231, and 241. That is, a boundary of the opening 221 defined in the substrate 22 may be spaced a predetermined distance from the left and right eyes of the user to prevent the light source of the substrate 22 from being disposed close to the left and right eyes of the user. The opening 241 defined in the wearing device 24 may have a size less than or equal to that of each of the remaining openings 211, 221, and 231 to effectively ensure the user's view.

The face contact 242 may be disposed along the boundary of the opening 241. When the user wears the optical output device 2, the face contact part 242 may include a first face contact part and a second face contact part, which are respectively contact the skin surface disposed around the user's left eye and the skin surface disposed around the user's right eye. As the face contact part 242 contacts the skin surface disposed around both the eyes of the user, the light emitted from the light source of the substrate 22 may be prevented from being irradiated to the user's eyes. The face contact part 242 may be made of a material such as rubber or silicon and may have an opaque color that minimizes light transmission.

The nose seating part 243 may be disposed between the first opening and the second opening, or between the first face contact part and the second face contact part and may be seated on the user's nose when the user is wearing. In order to be seated on the user's nose, the nose seating part 243 may be rounded to correspond to the shape of the person's nose.

The wearing fixing part 244 may be fixed to the user's body by being seated on the ear when the user is wearing or by being in close contact along the user's head. The optical output device 2 may be worn and fixed to the user's body by the nose seating part 243 and the wearing fixing portion 244.

The wearing detection sensor 245 may detect whether the optical output device 2 is worn on the user's body. For example, the wearing detection sensor 245 may be implemented as a proximity sensor. When the wearing detection sensor 245 is implemented as a proximity sensor, the proximity sensor may detect that a portion of the user's body (e.g., the face) approaches the proximity sensor as the optical output device 2 is worn. The proximity sensor may transmit a detection signal according to the proximity of a portion of the user's body to the controller (not shown) of the optical output device 2. The controller of the optical output device 2 may detect whether the optical output device 2 is worn based on the detection signal transmitted from the proximity sensor.

According to an embodiment, in order to prevent erroneous detection due to the proximity of another portion such as a user's hand when the user wears the optical output device 2 from occurring, the controller of the optical output device 2 may determine that the optical output device 2 is normally worn when the detection signal is continuously received for a predetermined time from the wearing detection sensor 245.

In some embodiments, during the wearing detection operation of the wearing detection sensor 245, the wearing detection operation may not be normally performed by the light emitted from the light source 222 (see FIG. 6) provided on the substrate 22 of the optical output device 2. For example, when the wearing detection sensor 245 is implemented as an infrared proximity sensor, the wearing detection sensor 245 may include a light source that emits infrared light and a light receiving part that receives reflected infrared light when the emitted infrared light is reflected by the human body or the like. When the wearing detection sensor 245 performs the emission and reception of the infrared light to detect whether the user is wearing, as the light emitted from the light source 222 is also received, the wearing detection operation may not be normally performed.

Accordingly, in order to solve the above problem, the optical output device 2 may include a filter (not shown) for blocking the light emitted from the light source 222 from being received by the wearing detection sensor 245. The filter may allow the infrared light to pass therethrough and block visible light (blue, yellow, red, etc.). For example, the filter may be provided to cover the wearing detection sensor 245 in FIG. 3 or may be disposed to be adjacent to the wearing detection sensor 245, but is not necessarily limited thereto.

The wearing detection sensor 245 may be electrically connected to the substrate 22 or may be electrically connected to the user operation device 4 through the substrate 22.

In particular, as illustrated in FIG. 3, the wearing detection sensor 245 may be disposed between the first opening and the second opening or between the first face contact part and the second face contact part and may be disposed above the nose seating part 243. That is, the wearing detection sensor 245 may be disposed to correspond to the forehead or a middle of the forehead when the user is wearing to detect the proximity of the forehead or the middle of the forehead of the user.

The face shape of the person may be different from each other, and a distance between the optical output device 2 and each portion of the face may also partially vary depending on the face shape. However, generally, when the optical output device 2 is worn, the distance between the optical output device 2 and the middle of the forehead may be relatively short depending on the face shape. Therefore, in the optical output device 2 according to an embodiment of the present disclosure, the wearing detection sensor 245 may be disposed at a position corresponding to the middle of the forehead of the user to effectively detect whether the user is wearing regardless of the user's face shape.

An example of the operation of the optical output device 2 according to whether the wearing detection sensor 245 is detected will be described later with reference to FIG. 11.

Referring to FIG. 4, the package 1 may further include a user operation device 4. The user operation device 4 may be connected to the optical output device 2 by a wire via a cable 421, but is not necessarily limited thereto. For example, the user operation device 4 may be wirelessly connected to the optical output device 2 through a wireless communication method. In this case, each of the substrate 22 and the user operation device 4 of the optical output device 2 may further include a wireless communication chip or element.

The user operation device 4 may provide an interface for allowing the user to turn on/off the power of the optical output device 2 or to set an operation mode of the optical output device 2.

A body part 41 of the user operation device 4 may be provided with a button part 411. For example, the button part 411 may include a power button for turning on/off the power of the optical output device 2 and an operation mode button for changing the operation mode of the optical output device 2. As illustrated in FIG. 4, in the button part 411, the power button and the operation mode button may be provided to be integrated with each other. In this case, one side of the button part 411 may correspond to the power button, and the other side may correspond to the operation mode button. According to an embodiment, the button part 411 may include a power button and an operation mode button, which are separated from each other. The user may turn on/off the power of the optical output device 2 or set the operation mode of the optical output device 2 by pressing a button 411.

The user operation device 4 includes an operation mode display part 412 for providing information on an operation mode that is currently set according to the operation of the button part 411 and a battery status display part 413 for providing information related to a battery state. The operation mode display part 412 and the battery status display part 413 may be implemented as LED light sources, but are not necessarily limited thereto.

In detail, the operation mode display part 412 may inform information on the currently selected operation mode to the user. For this, the operation mode display part 412 may include a plurality of operation mode display parts. As described above with reference to FIG. 2, it is assumed that the plurality of operation modes include an activity promotion mode for improving wrinkles, elasticity, and/or skin tone of the skin, and a trouble removal mode for removing trouble of the skin. In this case, a first operation mode display part of the plurality of operation mode display parts may correspond to the active promotion mode, and a second operation mode display part may correspond to the trouble removal mode. That is, when the currently selected operation mode is the active promotion mode, the first operation mode display part is activated to output light having a specific color (for example, red light), and when the currently selected operation mode is the trouble removal mode, the second operation mode display part may be activated to output light having a specific color (e.g., blue light).

The battery status display part 413 may visually provide information related to a remaining amount of battery to the user. For example, a color or a flickering cycle of the battery status display part 413 may be changed based on the remaining amount of battery.

For example, when the remaining amount of battery is greater than or equal to a reference amount, the color of the battery status display part 413 may be displayed as a first color (e.g., green), or the battery status display part 413 may not be flickered. On the other hand, when the remaining amount of battery is less than the reference amount, the color of the battery status display part 413 may be displayed as a second color (e.g., red), or the battery status display part 413 may be flickered.

As described above, the controller for controlling an overall operation of the optical output device 2 may be provided in the user operation device 4 instead of the substrate 22. In this case, the controller may be connected to the substrate 22 through a cable 421 to control operations of the light source provided on the substrate 22 or the wearing detection sensor 245 provided on the wearing device 24.

Although not shown, the user operation device 4 may be mounted to the cradle 3 when stored. In this case, the user operation device 4 may be connected to the cradle 3 through a connection terminal 422 to receive power from the cradle 3. According to an embodiment, a battery (not shown) for supplying power for the operation of the optical output device 2 as well as the user operation device 4 may be provided inside the user operation device 4. In this case, the battery may be charged by the power supplied from the cradle 3. Also, when the optical output device 2 operates, the battery may supply the power required for the operation.

Figure 5:
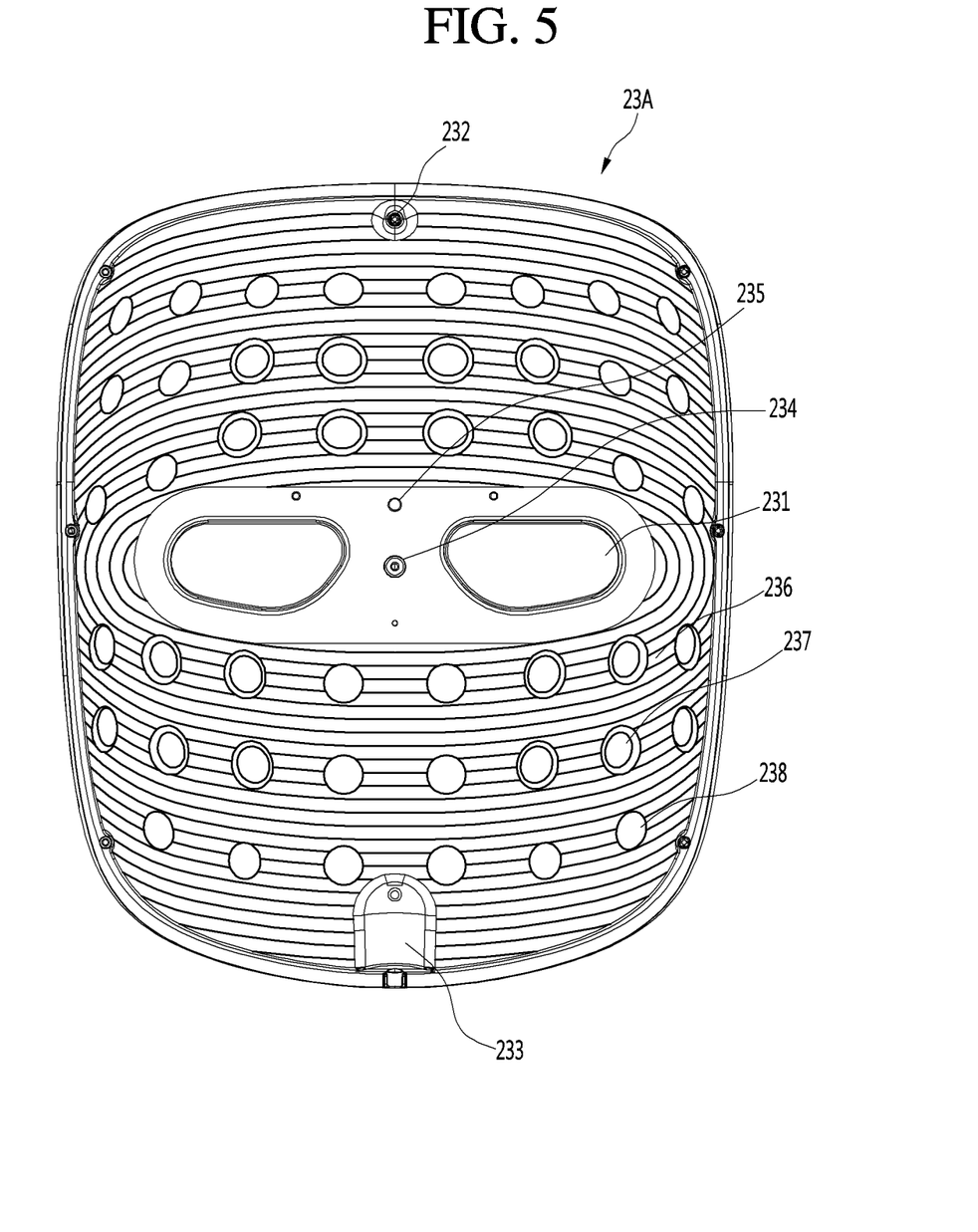
FIG. 5 is a front view illustrating an example of a rear cover provided in the optical output device for the skin care of FIG. 1.
Figure 6:
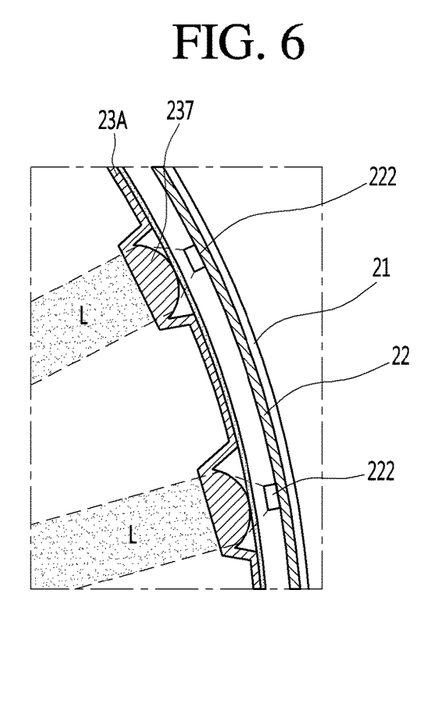
FIG. 6 is a cross-sectional view of the optical output device for the skin care, which includes the rear cover of FIG. 5.

FIG. 5 is a front view illustrating an example of the rear cover provided in the optical output device for the skin care of FIG. 1, and FIG. 6 is a cross-sectional view of the optical output device for the skin care, which includes the rear cover of FIG. 5.

Referring to FIG. 5, the rear cover 23A includes an opening 231, a coupling part 232, a connection part 233 for connecting the user operation device 4 to the substrate 22, and a wearing device coupling part 234, and a wearing detection sensor connection part 235.

As described above with reference to FIG. 2, the opening 231 may be provided to secure the user's view when the optical output device 2 is worn.

The rear cover 23A may be coupled to the front cover 21 and the substrate 22 through the coupling part 232. For example, the coupling part 232 may be constituted by a coupling hole and a screw passing through the coupling hole, but is not necessarily limited thereto. As the rear cover 23A is coupled to the front cover 21 and the substrate 22 through the coupling part 232, the substrate 22 may be protected by being surrounded by the front cover 21 and the rear cover 23A.

The wearing device 24 may be coupled to the rear cover 23 through the wearing device coupling part 234 of the rear cover 23. For example, as illustrated in FIG. 5, the wearing device coupling part 234 is implemented as a coupling groove having a specific shape, and the coupling device 24 is provided with the coupling part having a shape corresponding to that the coupling groove to couple the wearing device 24 to the rear cover 23. In FIG. 5, one wearing device coupling part 234 is provided on the rear cover 23, but a plurality of wearing device coupling parts may be provided according to an embodiment.

The wearing detection sensor connection part 235 may be provided to electrically connect the substrate 22 to the wearing detection sensor 245 or electrically connect the user operation device 4 to the wearing detection sensor 245. The wearing detection sensor connection part 235 may be disposed at a position corresponding to a position of the wearing detection sensor 245. For example, the wearing detection sensor connection part 235 may be implemented as a conductive contact pad or may be implemented as a connection hole through which a cable for connecting the wearing detection sensor 245 to the substrate 22 passes.

Referring to FIG. 5, a groove 236, a first lens 237, and a second lens 238 may be provided in the rear cover 23 according to an embodiment of the present disclosure.

A plurality of light sources may be spaced apart from each other on the substrate 22. For example, a distance between the light sources disposed on the substrate 22 may be determined based on a light irradiation angle of each of the light sources. For example, when arranging light sources arbitrarily without considering the light irradiation angle, the light emitted from the light sources may not be evenly irradiated on the user's skin, or unnecessary many light sources may be provided to reduce power efficiency. According to an embodiment of the present disclosure, the light sources are disposed on the substrate 22 based on the light irradiation angle of the light source to optimize the number of light sources disposed in the optical output device 2, thereby reducing unnecessary power consumption and improving efficiency of the skin care operation.

When the light is emitted from a plurality of light sources disposed spaced apart from each other, an intensity of the light irradiated to the skin, which is disposed at a position corresponding to a position at which the light source is disposed, may be greater than that of the light irradiated to the skin, which is disposed at a position corresponding to a position at which the light source is not disposed. That is, as the light is unevenly irradiated to the skin of the user, the skin care effect of the optical output device 2 may be deteriorated.

The wrinkles or troubles may be relatively largely generated when compared to the skin of other sites. For example, a number of wrinkles may be generated on the user's forehead when compared to other sites, and a number of freckles and the like may be generated on the cheeks of the user when compared to other sites. In this case, the optical output device 2 needs to maximize the skin care effect by irradiating more light to a specific site such as the user's forehead or cheek.

The groove 236 may be defined entirely in the remaining portions except for the lenses 237 and 238 of the rear cover 23 and the portion at which the wearing device 24 is mounted. For example, the groove 236 may provide the rear cover 23 having a bend or irregular surface so that the light emitted from the light source is dispersed when passing through the groove 236. As a result, the light may be more evenly irradiated to the user's skin to improve the skin care effect on various portions of the face.

The first lens 237 and the second lens 238 may be disposed on the rear cover 23 to correspond to the positions of a plurality of light sources disposed on the substrate 22. For example, the first lens 237 may be implemented as a convex lens, and the second lens 238 may be implemented as a planar lens.

In particular, the first lens 237 may be disposed to correspond to a portion having a relatively high probability of occurrence of the wrinkles or troubles such as the forehead or the cheek, i.e., a portion having the relatively high need for the skin care.

Referring to FIG. 6, when the light emitted from the light source 222 provided on the substrate 22 passes through the first lens 237, the emitted light may be refracted while passing through the first lens 237 so as to concentrated and irradiated to a predetermined area. That is, light L passing through the first lens 237 may be concentrated and irradiated to the skin area disposed at a position corresponding to the first lens 237. As the light is concentrated on the skin area as compared to other areas, the skin care effect may be improved.

When the light emitted from the light source 222 provided on the substrate 22 passes through the second lens 238, the emitted light is partially reflected when passing through the second lens 238, and thus, a portion of the light may pass through the second lens 238 as it is. The reflected light may be reflected again by the substrate 22 and then irradiated to the skin through the groove 236 or the like. According to an embodiment, the rear cover 23A may include only the groove 236 and the first lens 237.

That is, the light emitted from the light source 222 may be evenly irradiated to the skin by the grove 236 defined in the rear cover 23A. Also, the first lens 237 may be provided at a portion at which necessity or importance of the skin care is high, and the light emitted from the light source 222 may be concentrated and irradiated to the portion to improve the skin care effect.

Figure 7:
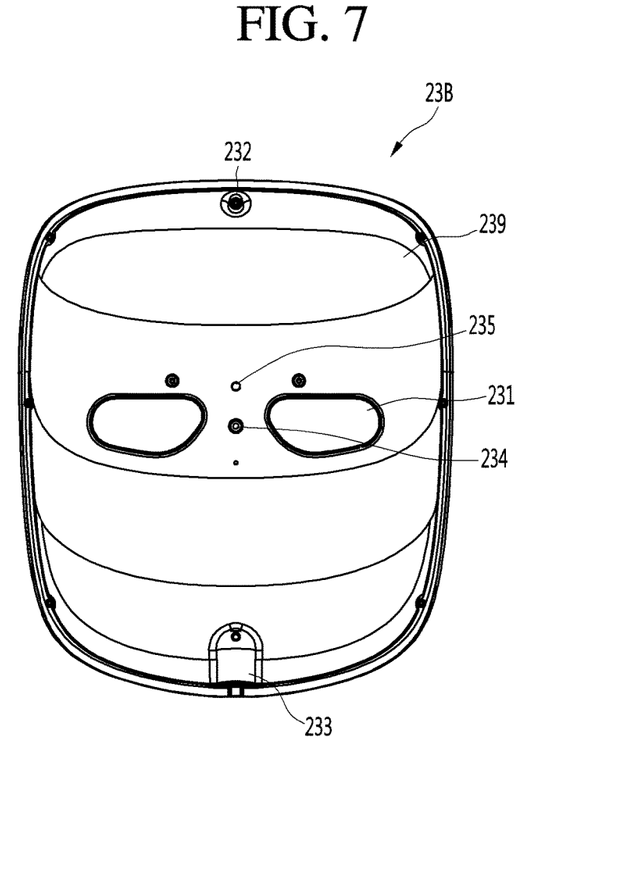
FIG. 7 is a front view illustrating another example of a rear cover provided in the optical output device for the skin care of FIG. 1.
Figure 8:
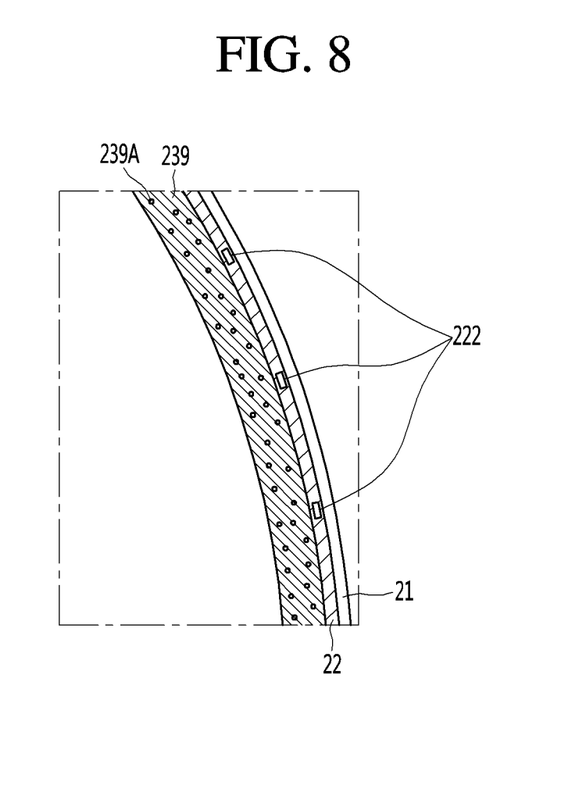
FIG. 8 is a cross-sectional view of the optical output device for the skin care, which includes the rear cover of FIG. 7.

FIG. 7 is a front view illustrating another example of the rear cover provided in the optical output device for the skin care of FIG. 1, and FIG. 8 is a cross-sectional view of the optical output device for the skin care, which includes the rear cover of FIG. 7.

Referring to FIGS. 7 and 8, the rear cover 23B may include a light guide layer 239 for evenly dispersing the light emitted from the light source 222 of the substrate 22. In FIGS. 7 and 8, only the light guide layer 239 is provided on the rear cover 23B. However, according to an embodiment, the first lens 237 of FIG. 5 and the light guide layer 239 may be provided on the rear cover 23B. In this case, the light guide layer 239 may be provided instead of the groove 236 and the second lens 238.

The light guide layer 239 may transmit the light emitted from the light source 222 toward the skin and simultaneously diffuse the light so that the light emitted from the light source 222 is uniformly provided toward the skin.

The light guide layer 239 may be made of a light transmissive material, for example, silicone or an acrylic resin. However, the material of the light guide layer 239 is not limited thereto. For example, the light guide layer 24 may be made of one of various resins. Also, a plurality of scattering particles 239A may be provided in the light guide layer 239. In detail, the scattering particles 239A may scatter or refract the light so that the light emitted from the light source 222 is spread more widely. As a result, the light may be irradiated more uniformly to the user's skin.

In order to scattering or refracting the light emitted from the light source 222, the scattering particles 239A may be made of a material having a refractive index different from that of the material forming the light guide layer 239, i.e., be formed of a material having a refractive index greater than that of a silicone-based or acrylic-based resin forming the light guide layer 24.

For example, the scattering particles 239A may include poly methyl methacrylate/styrene copolymer (MS), poly methyl metaacrylate (PMMA), poly styrene (PS), silicone, titanium dioxide (TiO2), silicon dioxide (SiO2), or a combination thereof.

The scattering particles 239A may be made of a material having a refractive index lower than that of the material constituting the light guide layer 239. For example, the scattering particles 239A may be constituted by bubbles in the light guide layer 233.

Figure 9:
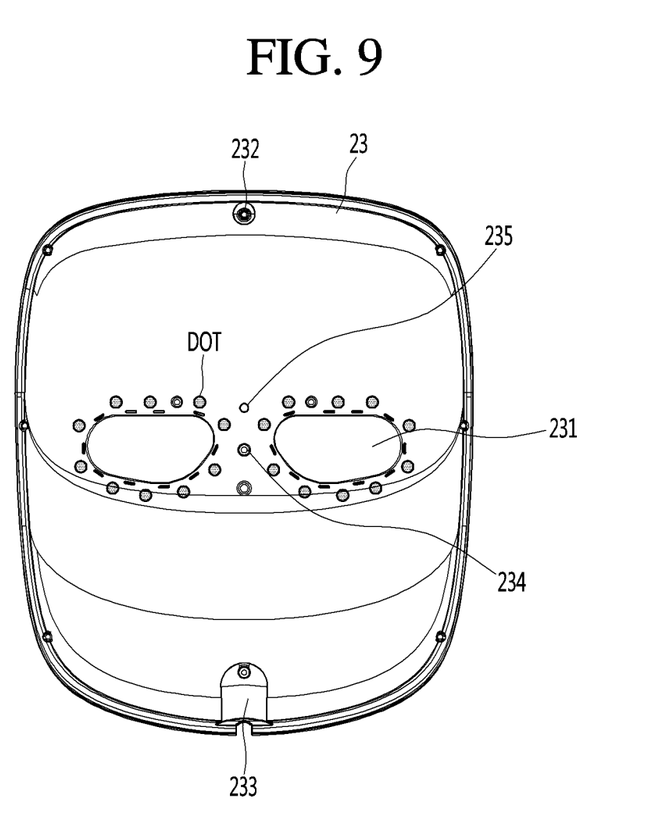
FIG. 9 is a front view illustrating an example of the rear cover provided in the optical output device for the skin care of FIG. 1.

FIG. 9 is a front view illustrating an example of the rear cover provided in the optical output device for the skin care of FIG. 1.

Referring to FIG. 9, the rear cover 23 may include a light absorption part DOT disposed along the boundary of the opening 231.

The light absorption part DOT may absorb the light emitted from the light source 222 and irradiated to be adjacent to the opening 231 to prevent the light emitted from the light source 222 from being irradiated directly or to be adjacent to the eye of the user through the boundary of the opening 231. Accordingly, as the light is irradiated to the eye when the optical output device 2 is used, it is possible to prevent the user from feeling uncomfortably or causing damage to the eye. The light absorption part DOT may be made of various materials having high light absorption properties such as polysilicon and gallium arsenide (GaAs).

As illustrated in FIG. 9, a plurality of light absorption parts DOT may be disposed to be spaced apart from each other along the boundary of the opening 231, but is not limited thereto. For example, in some embodiments, the light absorption parts DOT may be provided to surround the boundary of the opening 231.

Also, according to an embodiment, the rear cover 23 may be provided with a light transmission prevention part that prevents the light transmission instead of the light absorption portion DOT. The light transmission prevention part may prevent the light from being irradiated to or close to the eye of the user through the action such as the reflection of the light emitted from the light source.

In FIG. 9, the light absorption part DOT is disposed at a position close to the eye of the user, but it not limited thereto. For example, in some embodiment, the light absorption part DOT may be also disposed at a position corresponding to a mouth of the user to prevent the light from being irradiated to the mouth with a relatively weak skin, thereby preventing the risk of causing side effects.

Figure 10:
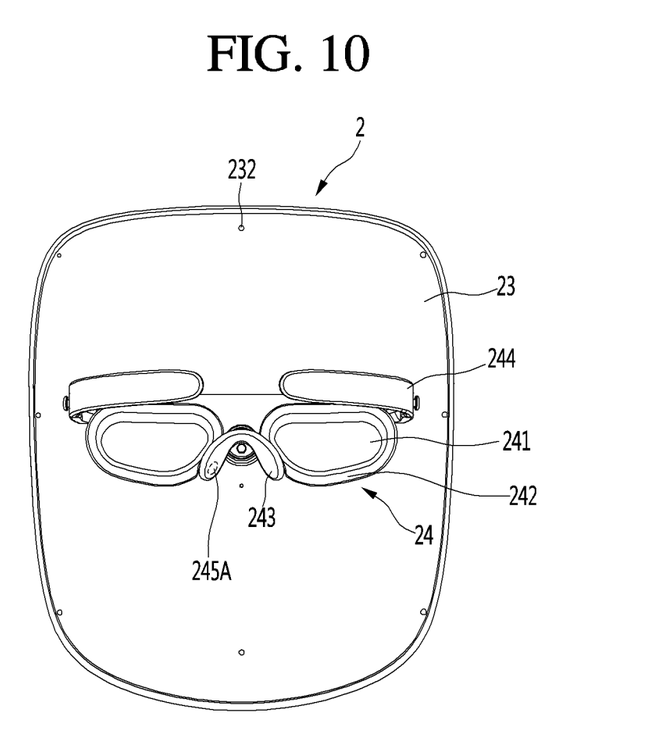
FIG. 10 is a rear view of the optical output device for the skin care so as to explain an additional example of an arrangement position of a wearing detection sensor of FIG. 3.

FIG. 10 is a rear view of the optical output device for the skin care so as to explain an additional example of an arrangement position of the wearing detection sensor of FIG. 3.

The wearing detection sensor 245 provided in the optical output device 2 according to an embodiment of the present disclosure may be disposed at a position other than a position corresponding to the user's forehead to detect whether the user is wearing.

As illustrated in FIG. 10, the wearing detection sensor 245A provided in the optical output device 2 may be disposed inside the nose seating part 243 or on the surface of the nose seating part 243. For example, when the wearing detection sensor 245A is implemented as a proximity sensor or a touch sensor, the wearing detection sensor 245A disposed inside the nose seating part 243 or on the surface of the nose seating part 243 may be worn by the user. When the nose seating part 243 may be in close proximity or contact with the user's nose, a detection signal may be transmitted to the controller. The controller provided in the optical output device 2 or the user operation device 4 may detect that the user has mounted the optical output device 2 by receiving the detection signal.

The nose seating part 243 may contact the nose of the user when worn, regardless of the face shape of the user. Therefore, when the wearing detection sensor 245A is disposed inside or on the surface of the nose seating part 243, the nose may contact the nose seating part 243 when the user is wearing to accurately detect whether the user is wearing when compared to other positions.

Similar to that described above with reference to FIG. 3, in order to prevent erroneous detection due to the proximity of another portion such as a user's finger when the user wears the optical output device 2 from occurring, the controller of the optical output device 2 may determine that the optical output device 2 is normally worn when the detection signal is continuously received for a predetermined time from the wearing detection sensor 245A.

In FIG. 10, only the embodiment in which the wearing detection sensor 245A is disposed on the nose seating part 243 is described. However, according to some embodiments, the wearing detection sensor 245A may be disposed at the other position (e.g., the face contact part 242, etc.) contacting a portion of the user's body when the user is wearing to minimize possibility of the erroneous detection according to a difference in user's face shape and to accurately detect whether or not to be worn.

Figure 11:
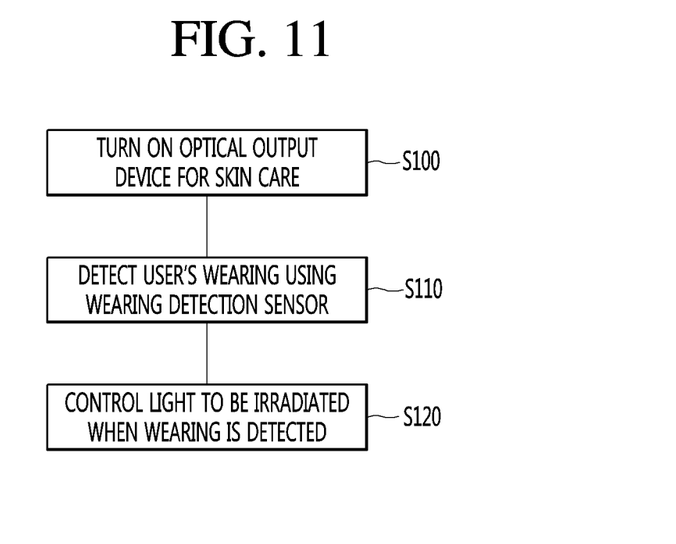
FIG. 11 is a flowchart for explaining an operation of the optical output device for the skin care according to an embodiment of the present disclosure.

FIG. 11 is a flowchart for explaining an operation of the optical output device for the skin care according to an embodiment of the present disclosure.

Referring to FIG. 11, the power of the optical output device 2 may be turned on by a user's operation (S100). For example, the user may turn on the power of the optical output device 2 by operating the power button of the button part 411 provided in the user operation device 4.

The optical output device 2 may detect whether the user wears the optical output device 2 by using the wearing detection sensor 245 (S110).

The controller of the optical output device 2 may activate the wearing detection sensor 245 when the power is turned on to detect whether the user wears the optical output device 2. Contents related to the wearing detection sensor 245 has been described above with reference to FIG. 3, and further description thereof will be omitted.

The controller may control the light source so as not to output the light until the user detects that the user wears the optical output device 2.

When the optical output device 2 detects that the user wears the optical output device 2, the optical output device 2 may control the light source to irradiate light to the user's skin (S120).

For example, the user may set the operation mode before wearing the optical output device 2 or set the operation mode after wearing the optical output device 2.

The user may set the operation mode in advance by operating the operation mode button of the button part 411 before wearing the optical output device 2. In this case, the controller of the optical output device 2 may control the light source to automatically output light corresponding to the set operation mode when the user's wearing is detected.

According to an embodiment, after the user wears the optical output device 2 and sets the operation mode by operating the operation mode button of the button part 411 provided in the user operation device 4, the controller of the optical output device 2 may control the light source to output light corresponding to the set operation mode.

That is, since the optical output device 2 controls the light so as not to be output before the user's wearing, it may be possible to prevent the user's discomfort or eye damage caused by the light being irradiated to the eyes during the user's wearing and effectively prevent the power from being unnecessarily consumed, thereby maximizing the user's satisfaction.

The above-disclosed subject matter is to be considered illustrative, and not restrictive, and the appended claims are intended to cover all such modifications, enhancements, and other embodiments, which fall within the true spirit and scope of the present disclosure.

Thus, the embodiment of the present disclosure is to be considered illustrative, and not restrictive, and the technical spirit of the present disclosure is not limited to the foregoing embodiment.

Therefore, the scope of the present disclosure is defined not by the detailed description of the disclosure but by the appended claims, and all differences within the scope will be construed as being included in the present disclosure.

The invention claimed is:

1. An optical output device for skin care, the optical output device comprising:
    a substrate disposed so that a plurality of light sources is oriented toward a user's skin;
    a front cover covering one surface of the substrate;
    a rear cover covering another surface of the substrate;
    a wearing device coupled to the rear cover to contact a portion of the user's body so that the optical output device is worn on the user; and
    a wearing detection sensor configured to detect whether the optical output device is worn by the user,
    wherein the rear cover comprises:
        a plurality of first lenses disposed in a first region of the rear cover corresponding to a portion of a forehead of the user's face and in a second region of the rear cover corresponding to a portion of cheeks of the face and configured to refract light emitted from the plurality of light sources such that the refracted light is irradiated to the forehead and the cheeks, each of the plurality of first lenses being a convex lens;
        a plurality of second lenses disposed in regions of the rear cover other than the first and second regions to pass some of the light emitted from the plurality of light sources, each of the plurality of second lenses being a planar lens; and
        a groove configured to disperse the light emitted from the plurality of light sources, and
    wherein:
    the groove is formed to have a bend or irregular surface on a portion of the rear cover other than portions of the rear cover on which the plurality of first lenses, the plurality of second lenses, and the wearing device are mounted; and the light emitted from the plurality of light sources is partially reflected when passing through the plurality of second lenses, and the reflected light is reflected again by the substrate and irradiated to the face through the groove.

2. The optical output device according to claim 1, wherein the wearing device comprises:

a first opening and a second opening, which are defined in positions corresponding to a left eye and a right eye, respectively, of the user;

a first face contact part and a second face contact part, which are disposed along boundaries of the openings to contact the skin of the user; and a nose seating part disposed between the openings so as to be seated on a nose of the user, wherein the wearing detection sensor is disposed between the first opening and the second opening.

3. The optical output device according to claim 2, wherein the wearing detection sensor is provided in the nose seating part or on a surface of the nose seating part.

4. The optical output device according to claim 1, wherein each of the substrate, the front cover, the rear cover, and the wearing device has an opening for securing a user's view, and the opening defined in the substrate has a size greater than or equal to a size of each of the openings defined in the front cover, the rear cover, and the wearing device.

5. The optical output device according to claim 1, further comprising a controller configured to:

control an operation of each of the at least one light source and the wearing detection sensor;

detect whether the user is wearing the optical output device based on a detection signal received from the wearing detection sensor; and cause the at least one light source to emit light based on a result of the detecting.

6. The optical output device according to claim 5, wherein the controller is provided on the substrate or in a user operation device connected to the substrate.

7. The optical output device according to claim 1, wherein the plurality of light sources are disposed to be spaced apart from each other on the substrate, and the plurality of light sources emit light differently based on an operation mode of the optical output device.

8. The optical output device according to claim 1, wherein the rear cover further comprises a light guide layer configured to scatter the light emitted from the at least one light source, and the light guide layer comprises a plurality of scattering particles.

9. The optical output device according to claim 1, wherein the rear cover further comprises an opening for securing the user's view, and at least one light absorption part is disposed along a boundary of the opening on a surface of both surfaces of the rear cover, which faces the substrate.

10. A skin care package comprising:

the optical output device for the skin care of claim 1;

a user operation device connected to the optical output device for the skin care, the user operation device comprising a button configured to set an operation mode of the optical output device for the skin care; and a cradle connected to the optical output device for the skin care and the user operation device to supply power for charging a battery provided in the optical output device for the skin care and the user operation device.

* * * * *